US009615902B2

(12) United States Patent
Miguel et al.

(10) Patent No.: US 9,615,902 B2
(45) Date of Patent: Apr. 11, 2017

(54) METHOD AND DEVICE FOR PRODUCING A DENTAL COMPONENT

(75) Inventors: Florent Miguel, Quebec (CA); Gilles Arnaud, Quebec (CA)

(73) Assignee: BIOCAD MEDICAL INC., Quebec (CA)

( * ) Notice: Subject to any disclaimer, the term of this patent is extended or adjusted under 35 U.S.C. 154(b) by 773 days.

(21) Appl. No.: 13/988,749

(22) PCT Filed: Nov. 18, 2011

(86) PCT No.: PCT/CA2011/001275
§ 371 (c)(1),
(2), (4) Date: Apr. 11, 2014

(87) PCT Pub. No.: WO2012/068667
PCT Pub. Date: May 31, 2012

(65) Prior Publication Data
US 2014/0250689 A1    Sep. 11, 2014

(30) Foreign Application Priority Data

Nov. 22, 2010 (GB) .................................. 1019699.6

(51) Int. Cl.
*A61C 5/10* (2006.01)
*A61C 13/00* (2006.01)
(Continued)

(52) U.S. Cl.
CPC ............ *A61C 13/0022* (2013.01); *A61C 5/10* (2013.01); *A61C 13/0006* (2013.01);
(Continued)

(58) Field of Classification Search
CPC ....... A61C 13/0022; A61C 5/10; A61C 13/12; A61C 13/0006; B23B 31/307; Y10T 29/49567; Y10T 29/49799; B23Q 3/00
See application file for complete search history.

(56) References Cited

U.S. PATENT DOCUMENTS 4,478,580 A * 10/1984 Barrut ...................... A61C 3/06
433/223
4,766,704 A    8/1988 Brandestini et al.
(Continued)

FOREIGN PATENT DOCUMENTS

CA    2330601 A1    12/1999
DE    87 09 853 U1    10/1987
(Continued)

OTHER PUBLICATIONS

International Search Report for Application No. PCT/CA2011/001275 issued Mar. 6, 2012 in 3 pages.
(Continued)

*Primary Examiner* — Sarang Afzali
*Assistant Examiner* — Ruth G Hidalgo-Hernande
(74) *Attorney, Agent, or Firm* — Knobbe, Martens, Olson & Bear LLP (57) ABSTRACT

The present disclosure relates to a method and device for producing a dental component. The method includes: a) providing a piece of material attached to or held by a first holder; b) shaping the piece of material to form the dental component and at least one support pin maintaining the dental component attached to the first holder or the initial piece of material; c) engaging a second holder to the dental component while the dental component still is attached to the first holder or the initial piece of material via the at least one support pin; and d) removing the at least one support pin from the dental component while the dental component is engaged by the second holder.

22 Claims, 6 Drawing Sheets

(51) Int. Cl.
  *A61C 13/12* (2006.01)
  *B23B 31/30* (2006.01)
(52) U.S. Cl.
  CPC ............ *A61C 13/12* (2013.01); *B23B 31/307* (2013.01); *Y10T 29/49567* (2015.01)

(56) References Cited

U.S. PATENT DOCUMENTS

| | | |
|---|---|---|
| 5,007,834 A | 4/1991 | Rubinstein et al. |
| 5,180,303 A | 1/1993 | Hornburg et al. |
| 6,287,121 B1 | 9/2001 | Guiot et al. |
| 6,485,849 B2 | 11/2002 | Petticrew |
| 6,547,649 B1 | 4/2003 | Andrus |
| 6,626,672 B1 | 9/2003 | Been |
| 6,640,150 B1 | 10/2003 | Persson et al. |
| 6,691,764 B2 | 2/2004 | Embert et al. |
| 6,818,573 B2 | 11/2004 | Petticrew |
| 6,915,178 B2 | 7/2005 | O'Brien et al. |
| 6,935,862 B2 | 8/2005 | Harlan |
| 7,092,780 B2 | 8/2006 | Ganley et al. |
| 7,144,240 B2 | 12/2006 | Maravilla |
| 7,217,130 B2 | 5/2007 | Giorno |
| 7,463,942 B2 | 12/2008 | O'Brien et al. |
| 7,670,142 B2 | 3/2010 | Giorno |
| 7,691,497 B1 | 4/2010 | Brodkin et al. |
| 7,708,557 B2 | 5/2010 | Rubbert |
| 7,735,542 B2 | 6/2010 | Marshall et al. |
| 7,754,115 B2 | 7/2010 | Veyrat |
| 8,231,825 B2 | 7/2012 | Eriksson et al. |
| 2002/0125619 A1 | 9/2002 | Bodenmiller et al. |
| 2002/0137002 A1 | 9/2002 | Bodenmiller |
| 2002/0162642 A1 | 11/2002 | Walker |
| 2004/0119180 A1 | 6/2004 | Frank |
| 2004/0137399 A1 | 7/2004 | Fleischfresser |
| 2004/0137408 A1 | 7/2004 | Embert et al. |
| 2005/0115460 A1 | 6/2005 | Petticrew |
| 2005/0146064 A1 | 7/2005 | Fecher et al. |
| 2005/0170315 A1 | 8/2005 | Strobel et al. |
| 2005/0202369 A1 | 9/2005 | Lee |
| 2005/0261795 A1 | 11/2005 | Ghosh et al. |
| 2005/0272008 A1 | 12/2005 | Stites |
| 2006/0082033 A1 | 4/2006 | Hauptmann et al. |
| 2007/0037127 A1 | 2/2007 | Ibsen et al. |
| 2007/0057391 A1 | 3/2007 | Ibsen et al. |
| 2008/0057101 A1 | 3/2008 | Roorda |
| 2008/0057102 A1 | 3/2008 | Roorda |
| 2008/0057103 A1 | 3/2008 | Roorda |
| 2008/0070191 A1 | 3/2008 | Ricks |
| 2008/0142183 A1 | 6/2008 | Marshall et al. |
| 2008/0206710 A1 | 8/2008 | Kruth et al. |
| 2008/0233542 A1 | 9/2008 | Procel |
| 2008/0254414 A1 | 10/2008 | McGuire et al. |
| 2009/0087818 A1 | 4/2009 | O'Brien et al. |
| 2009/0116915 A1* | 5/2009 | Kawasumi ............ B23B 3/065 483/14 |
| 2010/0015572 A1 | 1/2010 | Dierkes et al. |
| 2010/0042241 A1 | 2/2010 | Inoue |
| 2010/0133711 A1 | 6/2010 | Brodkin et al. |
| 2010/0203478 A1 | 8/2010 | Rubbert |
| 2010/0291509 A1 | 11/2010 | Berggren et al. |
| 2012/0326343 A1 | 12/2012 | Eriksson et al. |

FOREIGN PATENT DOCUMENTS

| | | |
|---|---|---|
| EP | 0086167 A2 | 8/1983 |
| EP | 1 088 620 A1 | 4/2001 |
| EP | 1127564 A2 | 8/2001 |
| EP | 1486181 A1 | 12/2004 |
| EP | 1543797 A1 | 6/2005 |
| EP | 2087852 A1 | 8/2009 |
| EP | 2087853 A1 | 8/2009 |
| EP | 2095789 A1 | 9/2009 |
| EP | 2 221 141 A2 | 8/2010 |
| GB | 649741 A | 1/1951 |
| JP | 05-329173 | 12/1993 |
| JP | 2000-052261 | 2/2000 |
| JP | 2002-173250 | 6/2002 |
| WO | WO 2006/031096 | 3/2006 |

OTHER PUBLICATIONS

Extended European Search Report for European patent application 11843021.4 dated Mar. 24, 2014.

* cited by examiner

METHOD AND DEVICE FOR PRODUCING A DENTAL COMPONENT

CROSS-REFERENCE TO RELATED APPLICATIONS

This application is a national stage application under 35 U.S.C. §371 of PCT Application No. PCT/CA2011/001275, filed on Nov. 18, 2011, which published in English as WO 2012/068667 A1 on May 31, 2012 and which claims priority benefit of GB Patent Application No. 1019699.6, filed on Nov. 22, 2010, the entire contents of which applications and publication are herein incorporated by reference in their entirety.

BACKGROUND

Field of the Invention

The present application relates to a method and device for producing a dental component.

Description of the Related Art

A dental component, such as a crown or bridge or (prosthetic) coping, may be produced by milling in a milling machine. First, a blank is attached to a holder or feeder in the milling machine. The dental component is then milled from the blank by removing material from the blank.

However, the dental component is not fully finished in the milling machine. There are typically one or more support pins that still maintains the dental component to the initial blank or holder. These support pins are then removed manually outside the milling machine, for instance by filing, grinding, and/or polishing. This manual removal is both time-consuming and difficult, and may result in that an outer surface of the dental component is not given the optimal properties it should have. The outer surface may even be damaged, and the produced dental component may have to be scrapped.

SUMMARY

It is an object of the present disclosure to at least partly overcome the above-mentioned drawbacks, and to provide an improved method and device for producing a dental component.

This, and other objects that will become apparent from the following description, is achieved by a method and device as defined in the appended independent claims. Example embodiments are set forth in the appended dependent claims.

According to an aspect of certain embodiments of the present disclosure, there is provided a method for producing a dental component, which method comprises: a) providing a piece of material attached to or held by a first holding means; b) shaping the piece of material to form the dental component and at least one support pin maintaining the dental component attached to the first holding means or the initial (remaining) piece of material; c) engaging a second holding means to the dental component while the dental component still is attached to the first holding means or the initial piece of material via the at least one support pin; and d) removing the at least one support pin from the dental component while the dental component is engaged by the second holding means.

Engaging the second holding means to the dental component makes the supporting pin(s) for maintaining the dental component superfluous, whereby the at least one support pin can be removed, and an end product without any support pins can be readily produced. In certain embodiments, there is no need to remove the support pin(s) manually, but the support pin(s) can instead be removed automatically, typically in the same machine that shaped the dental component. In this way, the support pin removal can be quick and accurate.

In some currently preferred embodiments, b) includes shaping the piece of material by milling and d) includes removing the at least one support pin by further milling, the shaping in b) and the removal in d) are made by the same equipment or tool, and/or the shaping in b) and the removal in d) are automated.

Further, c) may include engaging the second holding means in or to a cavity of the dental component. By engaging the second holding means in/to the cavity, there is, in various embodiments, substantially no risk that the second holding means will damage other portions of the dental component, such as the outer surface of the dental component.

The present method may further comprise: manufacturing or shaping the second holding means to at least partly fit with the cavity of the dental component. In some such embodiments, this allows the dental component to be firmly held in place during the subsequent removal of the support pin(s). The second holding means may for instance have an engaging portion that fully fits with the cavity of the dental component or that fits with only an opening portion of the cavity of the dental component.

Further, data for shaping the dental component may be used also for manufacturing or shaping the second holding means, which allows a perfect fit between the dental component and the second holding means in some embodiments.

The second holding means may be manufactured or shaped by one of: milling; rapid prototyping; molding or injecting a material directly in a cavity of the dental component; and molding or injecting a material in a cavity other than a cavity of the dental component.

Further, the dental component and/or the second holding means may be automatically positioned for engagement of the second holding means to the dental component by one of: keeping track of the positions of the dental component and the second holding means during the preceding operation(s); assigning specific positions to the dental component and the second holding means for the engagement; and using a detection means for detecting the actual positions of the dental component and the second holding means.

Further, the second holding means may be engaged to the dental component by suction through at least one hole on the second holding means, the suction creating a vacuum bringing the second holding means and the dental component together. In this way, the dental component can be firmly held by the second holding means, with minimum interference on the dental component. However, other solutions for engaging the dental component and the second holding means are also envisaged.

The dental component may be one of a crown, a bridge, and a coping.

Further, at least one of b), c), and d) may be controlled by a electronic control means, such as a microcontroller.

The second holding means may be manufactured or shaped before it is engaged to the dental component.

The at least one support pin may be shaped as at least one spoke.

According to another aspect of the present disclosure, there is provided a device adapted to perform the method according to the above description.

According to yet another aspect of the present disclosure, there is provided a device for producing a dental component, which device comprises: a first holding means adapted to maintain a piece of material by holding engagement or attachment; equipment adapted to shape the piece of material to form the dental component and at least one support pin maintaining the dental component attached to the first holding means or the initial (remaining) piece of material; one or more second holding means adapted to engage with the dental component; and equipment adapted to remove the at least one support pin from the dental component while the dental component is held by the one or more second holding means. This aspect may exhibit the same or similar features and technical effects as the previously described aspect of the disclosure.

The equipment adapted to remove the at least one support pin may be the same as the equipment adapted to shape the piece of material to form the dental component. Hence, the equipment adapted to shape the piece of material to form the dental component may further be adapted to (subsequently) remove the at least one support pin. Alternatively, a dedicated equipment for removing the support pints) may be used.

The device may be a milling machine and said equipment may be or include a milling tool.

The device may further comprise means for manufacturing or shaping the one or more second holding means to at least partly fit with a cavity of the dental component.

The device may further comprise means for automatically positioning the one or more second holding means for engagement to the dental component.

BRIEF DESCRIPTION OF THE DRAWINGS

These and other aspects of the present disclosure will now be described in more detail with reference to the appended drawings.

DETAILED DESCRIPTION

Figure 1:
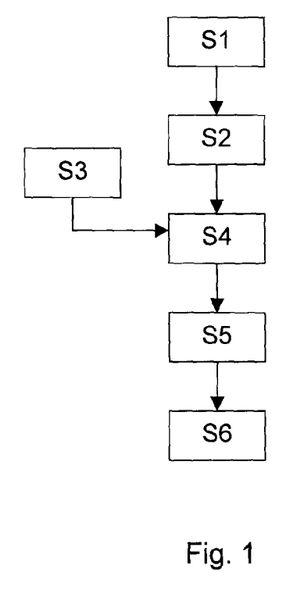
FIG. 1 is a flow chart of a method according to an example embodiment of the present disclosure.

FIG. 1 is a flow chart of a method for producing a dental component according to an example embodiment of the present disclosure. The dental component can for instance be a crown or a bridge or a (prosthetic) coping. In the following, certain embodiments of the present disclosure are described in the context of milling in a milling machine, though it is envisaged that other techniques could be used, such as rapid prototyping.

In step S1 in FIG. 1, a piece of material 10 is provided. The piece of material can be a blank (e.g., a cylinder, disc, bar, etc.) or a pre-manufactured shape. The pre-manufactured shape can for instance be made by rapid prototyping, custom powder pressing, etc. Further, the piece of material can be metal, ceramic, acrylic, glass, ceramic-glass, or other dental material.

Figure 2:
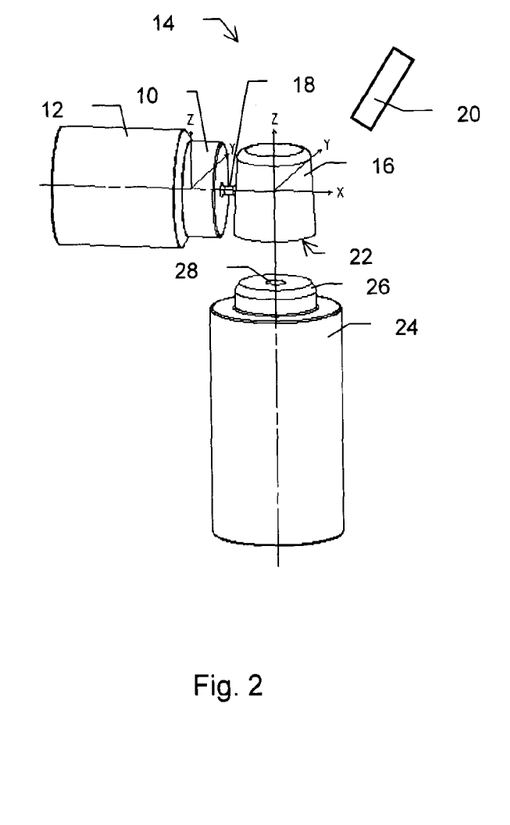
FIG. 2 is a perspective view of a device (e.g., a milling machine) according to an example embodiment of the present disclosure.

The piece of material 10 is attached to or held by a first holding means 12 in a milling machine 14 (see FIG. 2). The piece of material may for instance be for one dental component only, which piece of material can be glued or otherwise attached to the first holding means. Alternatively, the piece of material can be a feedable length of material from which several dental components can be produced. Such a feedable length of material can be held by a feeder, the feeder thus constituting said first holding means. Moreover, some embodiments of the present disclosure can also be used in conjunction with nesting technique for effectively milling a plurality of dental components from a larger blank.

In step S2, the piece of material is, for example, milled (e.g., shaped) to form a dental component 16 and at least one supporting pin 18, as seen in FIG. 2. Hence, the dental component 16 is at this stage not fully finished. The one or more support pins 18 maintain the dental component attached to the first holding means or to the remainder of the piece of material 10. The support pin(s) may for instance be on the outer side portion of the dental component, as in FIG. 2. Each support pin 18 may be discrete and shaped like a (thin, short) rod defining a point of attachment between the dental component 16 and the first holding means 12/remaining piece of material 10. In various embodiments, at least one pin 18 does not extend all around the component 16, allowing most of the component 16 to be shaped in step S2. Further, the at least one support pin 18 may be one or more (support) spokes, e.g., one or more small radiating bars.

In some embodiments, the milling is done by equipment of the milling machine 14, which equipment may include or comprise of a milling tool 20. For example, the milling tool 20 is automated, and shapes the dental component based on CAD data input to the milling machine. Preferably, the milling machine is set up for 5-axis milling, though also 3-axis milling may be used, for example.

The milled dental component 16 has a cavity 22. By means of the cavity 22, the final dental component can be fitted to a tooth or dental implant or abutment (on a dental implant) of a patient.

The present method may also comprise the step S3 of manufacturing or shaping a second holding means 24. The second holding means could also be referred to as a support die. The second holding means 24 is generally adapted to engage with the dental component 16, while the dental component still is attached to the first holding means or the remaining piece of material via the at least one support pin. Specifically, in various embodiments, the second holding means 24 should be able to maintain the dental component 16 in position, to allow further processing in the milling machine 14. To this end, the second holding means 24 can be manufactured or shaped to at least partly fit with the cavity 22 of the dental component 16, so that the second holding means 24 can be engaged in/to the cavity 22 of the dental component 16. This avoids unnecessary interaction with outer portions of the dental component 16 in some embodiments.

Figure 3A:
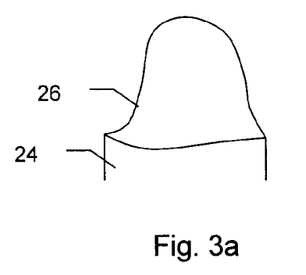
FIGS. 3a-3b are schematic side views of second holding means according to some embodiments of the present disclosure.
Figure 3B:
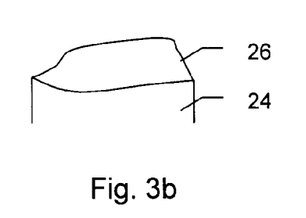
Figure 4A:
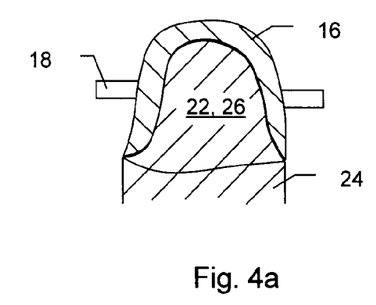
FIGS. 4a-4b are schematic cross-sectional side views of the second holding means of FIGS. 3a-3b engaged with a dental component.
Figure 4B:
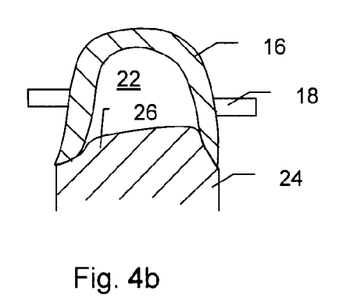

The second holding means 24 may have an engaging portion 26 that fully fits in the cavity 22 of the dental component, as shown in FIGS. 3a and 4a. That is, engaging portion 26 completely fills the cavity 22. Alternatively, engaging portion 26 of the second holding means 24 may fit with only an opening portion of the cavity 22 (see FIGS. 3b and 4b). Further, in various embodiments, the material used in the second holding means (particularly in the engaging portion 26 thereof) can be "hard" and perfectly match the shape of the dental component, or a little "soft" to adapt to a specific shape of the dental component. Preferably, in some embodiments, (CAD) data used for shaping the cavity of the dental component is used to manufacture or shape the second holding means, which allows a perfect fit between the dental component and the second holding means.

The manufacturing or shaping process for the second holding means can be milling, for instance in the same milling machine 14 used to shape the dental component. Alternatively, rapid prototyping (e.g., stereolithography or 3D printing) could be used. Instead of milling the second holding means or rapid prototyping it, the second holding means may be formed by molding or injecting a material directly into the cavity of the dental component or another cavity. To this end, a nozzle etc. (not shown) for the molding or injection could be integrated into the automation of the milling machine. The material molded or injected in the cavity could be a liquid that subsequently is frozen, a temporary glue or binder or gum, a low melting point metal, a polymerizable organic product, a foam, thermoplastic or thermosetting products, etc. The (final) material could be hard or somewhat soft or sticky. Also, it could be dense or porous. The latter may be especially beneficial for engaging the second holding means with the dental component, as will be explained further in the following.

The present method may further comprise the step S4 of positioning the dental component and/or the second holding means for engagement. The positioning can be made automatically by some apparatus in the milling machine, though it could alternatively be made manually by an operator. However, due to the fine dimensions and narrow tolerances usually involved in the production of a dental component, the former alternative is currently preferred, since it can be more accurate. The dental component and/or the second holding means may be automatically positioned or aligned for engagement of the second holding means to the dental component. This can be achieved by keeping track of the positions of the dental component and the second holding means during the preceding operation(s), e.g., the shaping of the dental component and the manufacturing/shaping of the second holding means. Alternatively, specific positions may be assigned to the dental component and the second holding means for the engagement. As yet another alternative, a detection means (e.g., a probe or scanning system, not shown) can be used for detecting the actual positions of the dental component and the second holding means. The positions of the dental component and the second holding means can be expressed as X, Y, and Z positions in the coordinate system shown in FIG. 2, and also as angular positioning around the X, Y, and Z axis.

It should be noted that when the second holding means is manufactured/shaped by molding or injection directly in the cavity of the dental component, step S4 may be omitted, since the second holding means is, in some embodiments, formed directly on the dental component. Further, when the second holding means is manufactured/shaped by molding or injection directly in the cavity of the dental component, this (i.e. step S3) must, in some embodiments, be performed after the dental product has been milled (step S2). Contrary, if the second holding means is manufactured/shaped in a different way, e.g., by milling or rapid prototyping, the second holding means can be manufactured/shaped before or simultaneously as the dental component is milled. This may save some time.

Figure 5:
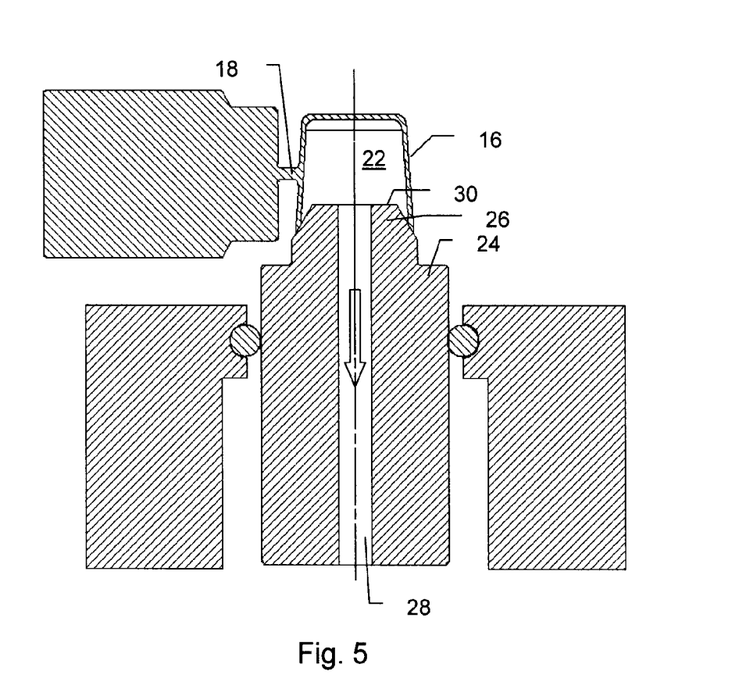
FIG. 5 is a cross-sectional side view of a second holding means engaged to a dental component according to an example embodiment of the present disclosure.

In step S5, the second holding means 24 is engaged or temporarily fastened to the dental component 16. In various embodiments, this is done while the dental component 16 still is attached to the first holding means or the remaining piece of material via the at least one support pin 18. In one example embodiment, the second holding means 24 includes at least one hole 28, as shown in FIG. 5. The hole 28 exits in a surface 30 of the engaging portion 26 of the second holding means 24, which surface 30 is in communication with the cavity 22 of the dental component 16. By sucking air out from the cavity 22 through the hole(s) 28 (indicated by downward pointing arrow in FIG. 5) by means of a suction device (not shown), a vacuum, in some embodiments, is created that brings the second holding means 24 and the dental component 16 together, whereby the dental component 16 is firmly held by the second holding means 24. The end opening of the hole 28 towards the dental component 16 is also shown in FIG. 2. In case the second holding means 24 is porous as mentioned above, no dedicated hole(s) 28 may be necessary to allow suction.

Alternatives or complements for maintaining the dental component 16 on top of the second holding means 24 include, but are not limited to:

the mere shape of the engaging portion of the second holding means fits with the shape of the cavity, so that the dental component is maintained on the second holding means;

a foam is pressing the dental component towards the second holding means;

two foam fingers pinch the dental component vertically; and freezing the dental component on the second holding means, for instance by adding some liquid on the contact surface between the dental component and the second holding means and freezing the liquid to stick the two items together.

Figure 6A:
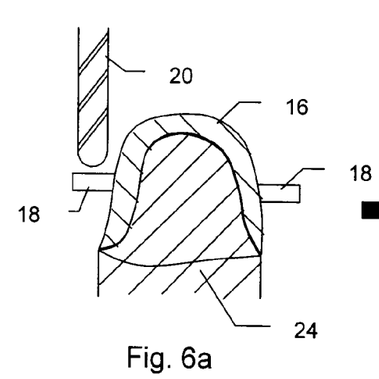
FIGS. 6a-6c are schematic partly cross-sectional side views showing pin removal and a resulting dental component according to certain embodiments of the present disclosure.
Figure 6B:
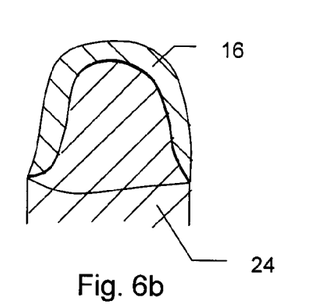

Once the second holding means 24 is engaged to the dental component 16, the at least one support pin 18 may be removed 18 in step S6, as showed in FIGS. 6a-6b. It will be appreciated that the support pin(s) 18 no longer is/are necessary to hold the dental component 16, in various embodiments, since the latter at this stage (also) is held in place by the second holding means 24. The pin(s) 18 may therefore be removed at this stage. The same milling tool 20 that was used to mill the dental component in step 32 may be used also to remove the support pin(s) 18. Alternatively, another milling tool of the milling machine 14 could be used for the pin removal, for example.

The milling tool 20 (both for shaping of the dental component and removal of the pin(s)) and the positioning and engagement of the second holding means may be controlled by an electronic control means (not shown) of the milling machine 14.

Figure 6C:
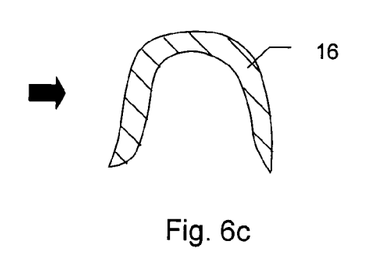

The output of step S6 is hence a fully milled dental component 16' without any support pin(s). It is appreciated that no manual removal of the support pin(s) is required in various embodiments, whereby the quality of the output dental component may be improved. Once the dental component is fully milled, it can be step out of the milling machine 14 alone (FIG. 6c) or with the second holding means 24. If additional means (e.g., suction means or foam)

has been used to maintain the dental component to the second holding means, they can be disabled or released at this stage or later.

Figure 7:
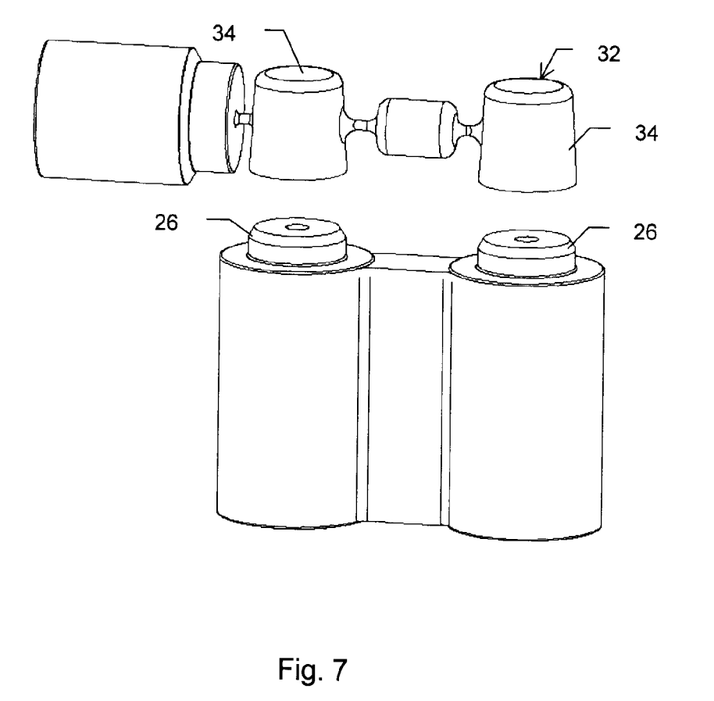
FIG. 7 is a perspective view of a device (e.g., a milling machine) according to another embodiment of the present disclosure.

In case the dental component to be milled is a bridge 32 having several supporting teeth 34 (see FIG. 7), the second holding means can be configured with one engaging portion 26 for each supporting tooth 34. Alternatively, additional second holding means 24 of the type discussed above in relation to, e.g., FIG. 2 can used, for instance one second holding means 24 for each supporting tooth of the bridge. As yet another alternative, only one of bridge's supporting teeth may be engaged by the second holding means.

The person skilled in the art realized that the present invention by no means is limited to the embodiments described above. On the contrary, many modifications and variations are possible within the scope of the appended claims.

What is claimed is:

1. A method for producing a dental component, the method comprising:
   a) providing a piece of material attached to or held by a first holder;
   b) shaping the piece of material to form the dental component and at least one support pin maintaining the dental component attached to the first holder, wherein the at least one support pin defines a point of attachment between the dental component and a remaining of the piece of material attached to or held by the first holder;
   c) engaging a second holder to hold the dental component while the dental component still is attached to the first holder; and
   d) removing the at least one support pin from the dental component while the dental component is engaged and held by the second holder.

2. The method according to claim 1, wherein the shaping in b) includes shaping the piece of material by milling, and wherein the removing in d) includes removing the at least one support pin by further milling.

3. The method according to claim 1, wherein the shaping in b) and the removing in d) are performed by a same equipment or tool.

4. The method according to claim 1, wherein the shaping in b) and the removing in d) are automated.

5. The method according to claim 1, wherein the engaging in c) includes engaging the second holder in or to a cavity of the dental component.

6. The method according to claim 5, further comprising: manufacturing or shaping the second holder to at least partly fit with the cavity of the dental component.

7. The method according to claim 5, wherein the second holder has an engaging portion that fully fits with the cavity of the dental component or that fits with only an opening portion of the cavity of the dental component.

8. The method according to claim 1, wherein data for shaping the dental component is used also for manufacturing or shaping the second holder.

9. The method according to claim 1, wherein the second holder is manufactured or shaped by:
   milling;
   rapid prototyping;
   molding or injecting a material directly in a cavity of the dental component; or
   molding or injecting a material in a cavity other than a cavity of the dental component.

10. The method according to claim 1, wherein the dental component or the second holder is automatically positioned for engagement of the second holder to the dental component by:
    keeping track of positions of the dental component and the second holder during a preceding operation;
    assigning specific positions to the dental component and the second holder for the engagement; or
    detecting actual positions of the dental component and the second holder.

11. The method according to claim 1, wherein the second holder is engaged to the dental component by suction through at least one hole on the second holder, the suction creating a vacuum bringing the second holder and the dental component together.

12. The method according to claim 1, wherein the dental component is a crown, a bridge, or a coping.

13. The method according to claim 1, wherein b), c), or d) is controlled electronically.

14. The method according to claim 1, wherein the second holder is manufactured or shaped before it is engaged to the dental component.

15. The method according to claim 1, wherein the at least one support pin is shaped as at least one spoke.

16. A device adapted to perform the method according to claim 1.

17. The method according to claim 1, wherein the piece of material is attached to or held by the first holder along a first axis, and the second holder is engaged to the dental component along a second axis different than the first axis.

18. A device for producing a dental component, the device comprising:
    a) a first holder adapted to maintain a piece of material by holding engagement or attachment;
    b) an equipment adapted to shape the piece of material to form a dental component and at least one support pin maintaining the dental component attached to the first holder, wherein the at least one support pin defines a point of attachment between the dental component and a remaining of the piece of material attached to or held by the first holder;
    c) one or more second holders adapted to engage and hold the dental component while the dental component is still attached to the first holder; and
    d) an equipment adapted to remove the at least one support pin from the dental component while the dental component is held by the one or more second holders.

19. The device according to claim 18, wherein the device is a milling machine and said equipment adapted to shape or said equipment adapted to remove includes a milling tool.

20. The device according to claim 18, further comprising equipment adapted to manufacture or shape the one or more second holders to at least partly fit with a cavity of the dental component.

21. The device according to claim 18, further comprising an equipment adapted to automatically position the one or more second holders for engagement to the dental component.

22. The device according to claim 18, wherein the first holder is adapted to maintain the piece of material along a first axis, and one of the second holders is adapted to engage with the dental component along a second axis different than the first axis.

* * * * *

UNITED STATES PATENT AND TRADEMARK OFFICE
CERTIFICATE OF CORRECTION

PATENT NO. : 9,615,902 B2
APPLICATION NO. : 13/988749
DATED : April 11, 2017
INVENTOR(S) : Florent Miquel Page 1 of 1

It is certified that error appears in the above-identified patent and that said Letters Patent is hereby corrected as shown below:

On the Title Page

Item (75), Inventors at Line 1, Change "Florent Miguel," to --Florent Miquel,--.

Signed and Sealed this
Tenth Day of July, 2018

Andrei Iancu
*Director of the United States Patent and Trademark Office*